US00PP29369P2

(12) United States Plant Patent
Thompson

(10) Patent No.: US PP29,369 P2
(45) Date of Patent: Jun. 12, 2018

(54) RASPBERRY PLANT NAMED 'PBBRASP1381'

(50) Latin Name: ***Rubus idaeus* L.**
Varietal Denomination: PBBrasp1381

(71) Applicant: Pacific Berry Breeding, LLC, Salinas, CA (US)

(72) Inventor: Ellen Thompson, Watsonville, CA (US)

(73) Assignee: Pacific Berry Breeding, Salinas, CA (US)

( * ) Notice: Subject to any disclaimer, the term of this patent is extended or adjusted under 35 U.S.C. 154(b) by 0 days. days.

(21) Appl. No.: 15/731,006

(22) Filed: Apr. 5, 2017

(51) Int. Cl.
*A01H 5/08* (2018.01)

(52) U.S. Cl.
USPC ..... Plt./204

(58) Field of Classification Search
USPC ..... Plt./204
See application file for complete search history.

*Primary Examiner* — Annette H Para
(74) *Attorney, Agent, or Firm* — King IP Law; Joshua King

(57) ABSTRACT

The present application relates to a new and distinct cultivar of primocane-fruiting raspberry named 'PBBrasp1381'. The new variety reliably provides balanced heavy crop load on both primocanes and floricanes, with jumbo, firm, glossy, medium-colored conic fruits of loose adherence to the receptacle and which maintain size throughout harvest. Plants possess high vigor and produce high numbers of spawn. Improved resistance to yellow rust (*Phragmidium rubi-idaei*), and field tolerance to Raspberry Bushy Dwarf Virus (RBDV) and *Phytophthora* root rot has been observed.

5 Drawing Sheets

Latin name of the genus and species of the plant claimed: *Rubus idaeus* L.

Variety denomination: 'PBBrasp1381'.

BACKGROUND AND SUMMARY

The new primocane-fruiting raspberry cultivar designated as 'PBBrasp1381' is described herein. Botanically known as *Rubus idaeus* L., this new variety resulted from a hand-pollinated cross of female parent 'Pacific Gema' (U.S. Plant Pat. No. 28,080), a release from the same program, and the male parent 'Pacific Starlet' (U.S. Plant Pat. No. 28,046). Pollination occurred in April 2012 and seeds from this controlled cross were subsequently harvested, cleaned, germinated, and established as seedlings in spring 2013 in Watsonville, Calif., Santa Cruz County, USA.

'PBBrasp1381' was first identified in a substrate block, where seedlings had individually been planted into 3 liter pots, in September 2013 in Watsonville, Calif. This selection was first propagated asexually by crown division (of the original potted mother-plant) in autumn 2013 in Watsonville, Calif. The crown on the original plant was parted into basal cane pieces (approximately 15 cm long) with root attached and planted into soil, in a selection plot elsewhere on the farm, resulting in a 10-fold increase in plant material. Harvest and postharvest data were collected from this larger plot of 'PBBrasp1381' for two years, from 2014 through 2016.

In January 2014, additional root pieces from the original mother-plant were planted into an on-site greenhouse. Two actively growing etiolated shoots were forced from roots, transplanted and potted. Once established, these shoots were sent to Lafayette, Oreg., USA, where vegetative material was explanted and established in vitro for micropropagation. Subsequent asexual propagation was done on-site in Watsonville, Calif. and, along with tissue-cultured plantlets, 'PBBrasp1381' was evaluated extensively over the next several years for performance and genetic stability.

The present cultivar, 'PBBrasp1381' offers many advantages over the existing cultivar and maternal parent, 'Pacific Gema' (U.S. Plant Pat. No. 28,080). Particularly for average fruit size, 'PBBrasp1381' is noteworthy, for it is considered a jumbo berry and is much larger than 'Pacific Gema', on average. Further, berries are extremely firm and detach more easily from the receptacle than 'Pacific Gema'. Berries of 'PBBrasp1381' are more broadly-conic and elongate in shape (versus the narrow conic shape of 'Pacific Gema'). Yield of 'PBBrasp1381' is also greater than 'Pacific Gema', on average, due to its superior vigor and berry weight. The ease of fruit detachment and improved yield offers significant advantages to growers, who require fast picking speeds to maintain harvest efficiency. Fruit color and gloss of 'PBBrasp1381' are similar to that of 'Pacific Gema'. In addition, root vigor and floricane budbreak for 'PBBrasp1381' is superior over 'Pacific Gema'.

In contrast to the male parent 'Pacific Starlet' (U.S. Plant Pat. No. 28,046), the present cultivar is significantly greater in vigor, plant fitness and offers larger fruit. In particular, the amount of suckers that 'PBBrasp1381' produces is two-fold of its paternal parent. This improvement is of significant importance to growers, who rely upon the regenerative ability of suckers, in order to guarantee subsequent crops. Floricane budbreak of 'PBBrasp1381' is more consistent than 'Pacific Starlet', leading to more reliable spring crops and a balanced cropload among floricane and primocane cycles.

Thus, these characteristics help define 'PBBrasp1381' as a new and distinct cultivar of primocane-fruiting raspberry. 'PBBrasp1381' may be recognized by its high vigor, strong suckering habit, uniform floricane budbreak, extreme vigor and firmness, large broadly-conic berries of jumbo size and high gloss, and which consistently yield more than existing parental varieties within the same program.

BRIEF DESCRIPTION OF THE PHOTOGRAPHS

DETAILED DESCRIPTION

Figure 1:
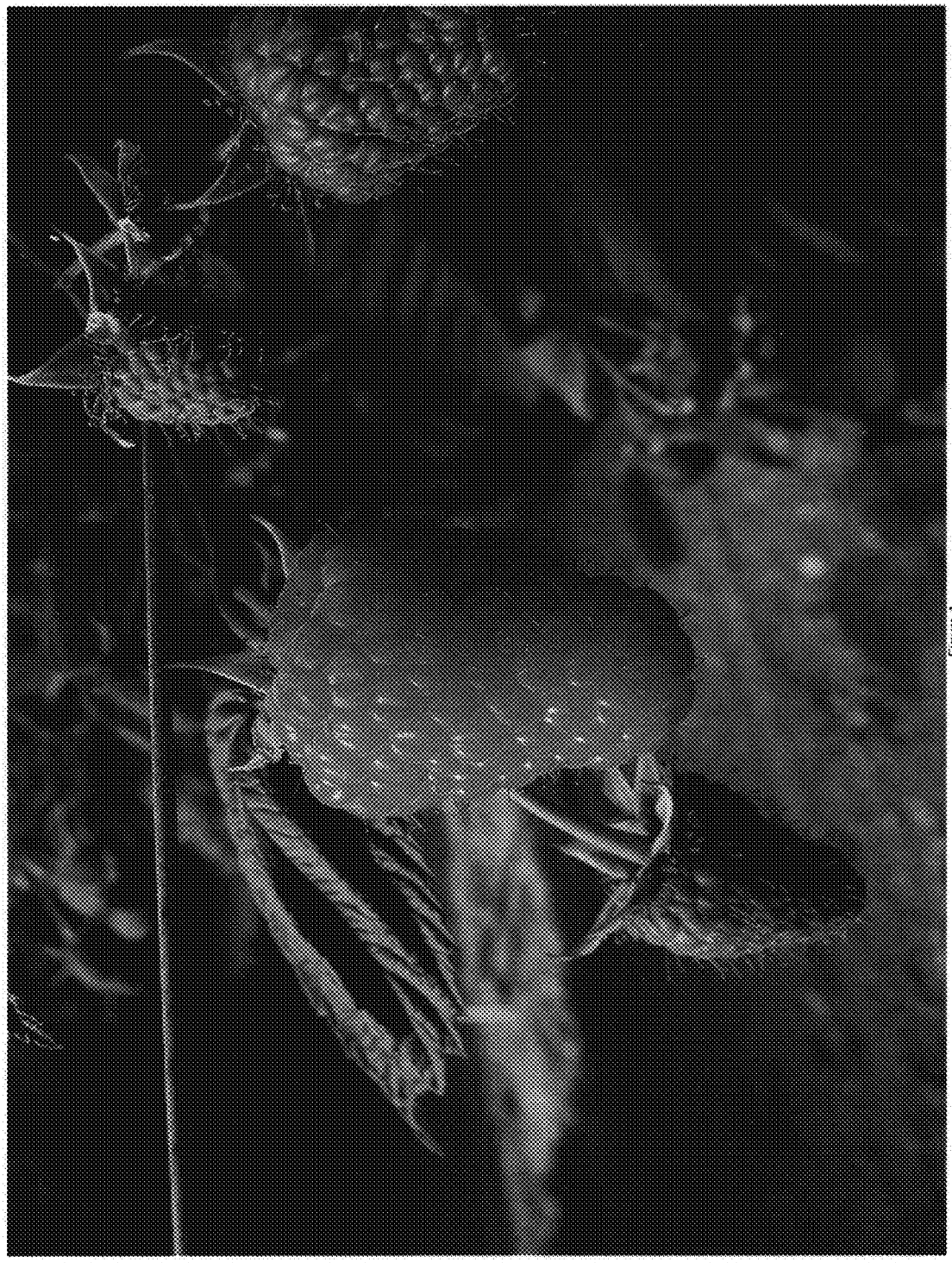
FIG. 1 is a photograph showing the fresh fruit color of raspberry cultivar 'PBBrasp1381'.
Figure 2:
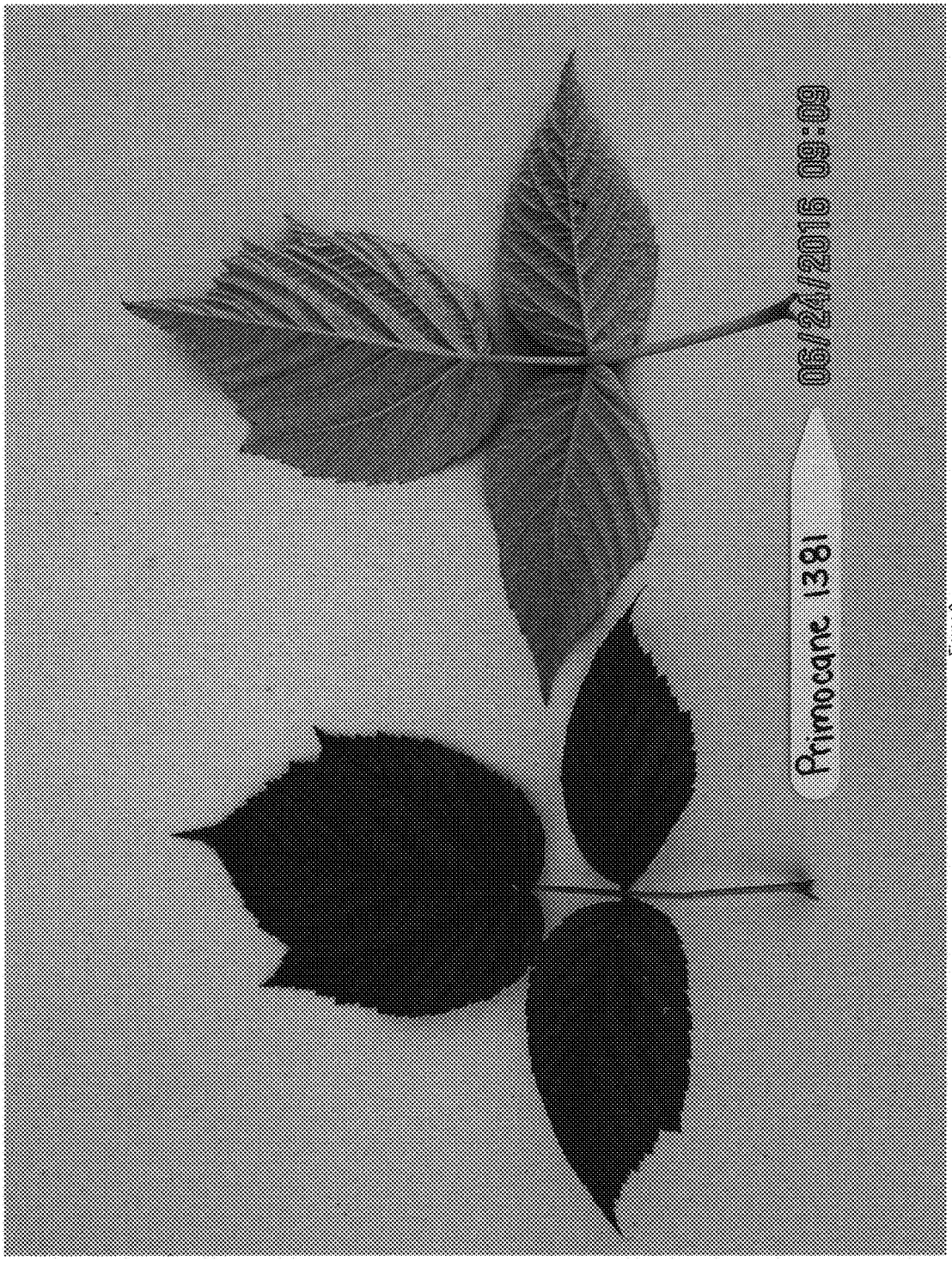
FIG. 2 is a photograph displaying primocane leaf size and morphology of raspberry cultivar 'PBBrasp1381'.
Figure 3:
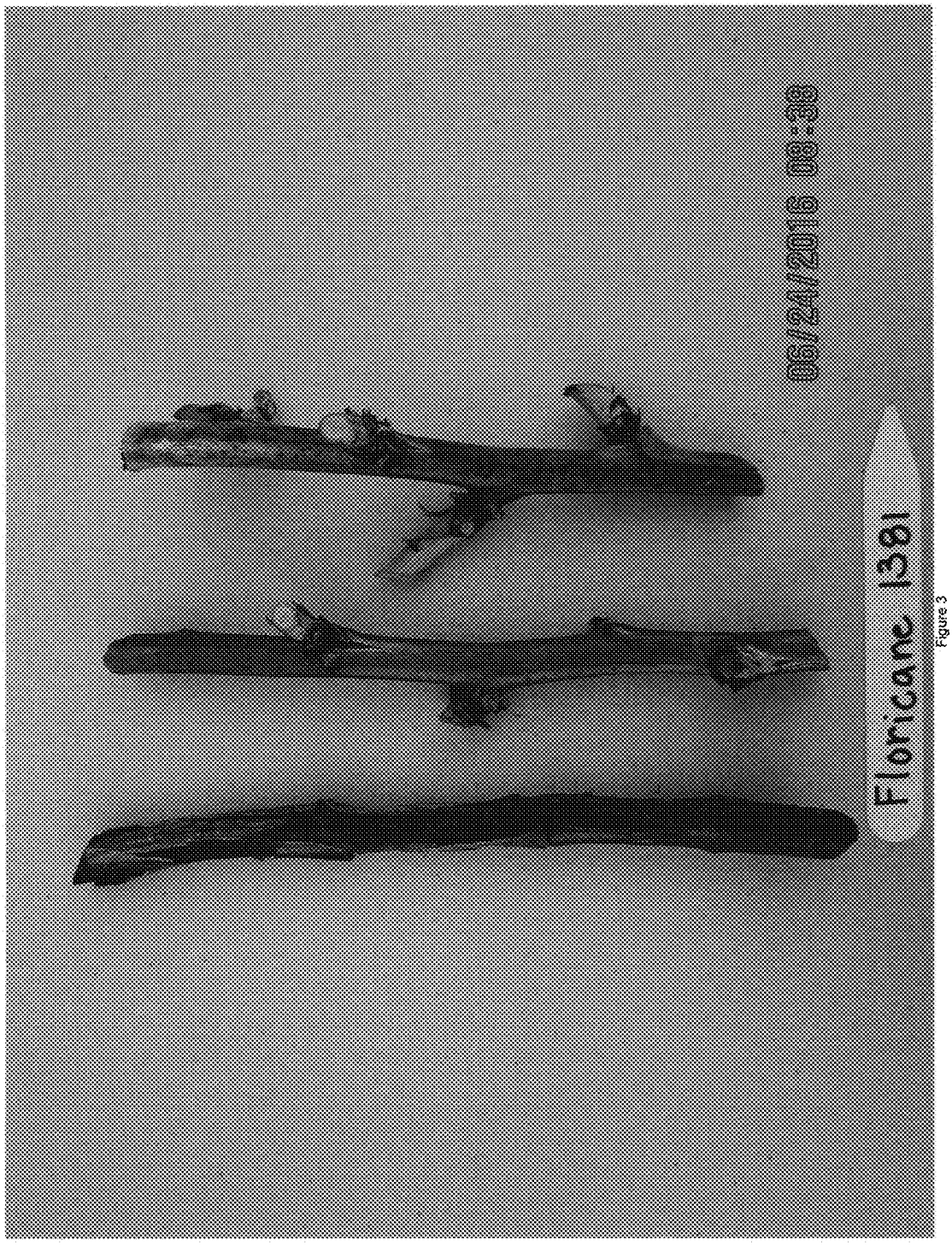
FIG. 3 is a photograph showing the cane and spine color of raspberry cultivar 'PBBrasp1381' on its floricanes.
Figure 4:
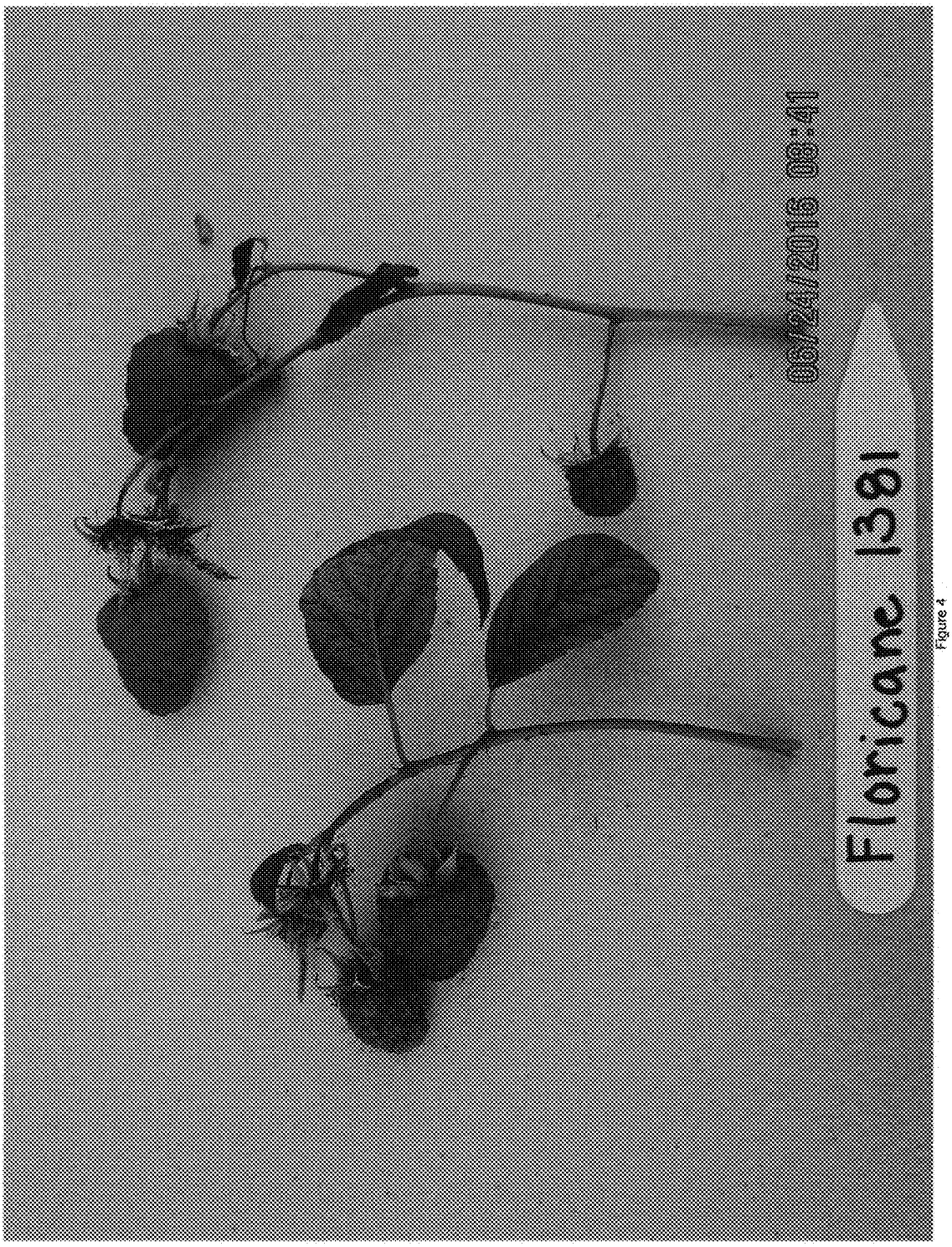
FIG. 4 is a photograph showing inflorescence morphology and fruit development of raspberry cultivar 'PBBrasp1381'.
Figure 5:
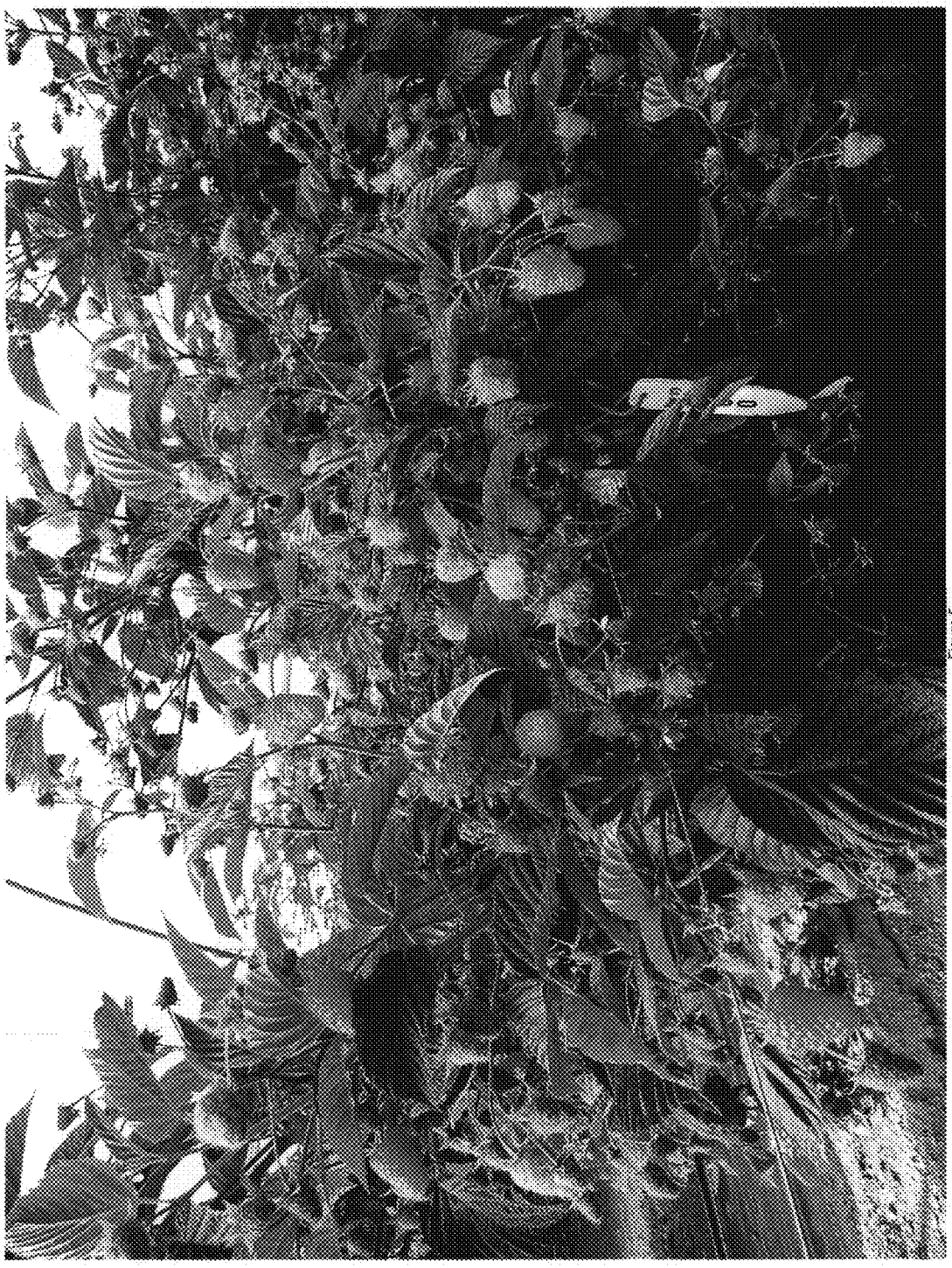
FIG. 5 is a photograph displaying the canopy, primocane crop load and architectural habit of raspberry cultivar 'PBBrasp1381'.

Note: Statements of characteristics herein represent exemplary observations of the cultivar herein and will vary depending on time of year, location, annual weather, etc.

Cultivar name: 'PBBrasp1381'.

Classification:

*Family*.—Rosaceae.

*Botanical name*.—*Rubus idaeus* L.

*Common name*.—Raspberry.

Parentage:

*Female parent*.—'Pacific Gema' (U.S. Plant Pat. No. 28,080).

*Male parent*.—'Pacific Starlet' (U.S. Plant Pat. No. 28,046). As noted above, compared to the maternal parent, 'Pacific Gema', present cultivar, 'PBBrasp1381' offers many advantages. Particularly for average fruit size, 'PBBrasp1381' is noteworthy, for it is considered a jumbo berry and is much larger than 'Pacific Gema' on average. Further, berries are extremely firm and detach more easily from the receptacle than 'Pacific Gema'. Berries of 'PBBrasp1381' are more broadly-conic and elongate in shape (versus the narrow conic shape of 'Pacific Gema'). Yield of 'PBBrasp1381' is also greater than 'Pacific Gema', on average, due to its superior vigor and berry weight. The ease of fruit detachment and improved yield offers significant advantages to growers, who require fast picking speeds to maintain harvest efficiency. Fruit color and gloss of 'PBBrasp1381' are similar to that of 'Pacific Gema'. In addition, root vigor and floricane budbreak for 'PBBrasp1381' is superior over 'Pacific Gema'. Compared to the patented male parent 'Pacific Starlet' (U.S. Plant patent application Ser. No. 14/544,826, filed Feb. 24, 2015), the present cultivar is significantly greater in vigor, plant fitness and offers larger fruit. In particular, the amount of suckers that 'PBBrasp1381' produces is two-fold of its paternal parent. This improvement is of significant importance to growers, who rely upon the regenerative ability of suckers, in order to guarantee subsequent crops. Yield, firmness and overall plant fitness of 'PBBrasp1381' also outperform other previous releases from this same program, including 'Pacific Deluxe' (U.S. Plant Pat. No. 21,074), 'Pacific Royale' (U.S. Plant Pat. No. 21,536), and 'Pacific Majesty' (U.S. Plant Pat. No. 47,306). Thus, these characteristics help define 'PBBrasp1381' as a new and distinct cultivar of primocane-fruiting raspberry. 'PBBrasp1381' may be recognized by its high vigor, strong suckering habit, uniform floricane budbreak, extreme vigor and firmness, large broadly-conic berries of jumbo size and high gloss, and which consistently yield more than existing varieties within the same program.

Growing location for the observations herein: Watsonville, Calif., USA.

Time of year (season): Early summer for floricanes, and late summer for primocanes.

Age of plants used for this discussion: Crown age of about 2 years; floricane age 18 months; primocane age 8 months.

Age of plants used for the photographs in the figures: Crown age of about 2 years; floricane age 18 months; primocane age 8 months.

Type of greenhouse covering or growing structure, or field: High tunnel over field-grown plants.

Light: Natural.

Color terminology refers to The R.H.S. Colour Chart, Royal Horticultural Society, Fifth Edition, London, United Kingdom (2007).

Observations for floricanes herein were made in June 2016. Observations for primocanes herein were made in August 2016.

Plant:

*Form/shape*.—Vase.

*Growth habit*.—Erect.

*Height*.—2.4 m, as measured from cane base to apex.

*Spread*.—0.5 m as measured from terminal leaflet tip to terminal leaflet tip.

*Propagation methods*.—Division.

*Time to initiate and develop roots*.—24 days.

*Root description*.—Fibrous. Generally of medium diameter with a smooth, glossy texture.

Primocanes:

*Cane diameter*.—Base: 0.9 cm | Middle: 0.9 cm | Tip: 0.6 cm.

*Cane length*.—1.6 m.

*Number of node per cane*.—24.

*Internode length*.—Base: 6.8 cm | Middle: 10.1 cm | Tip: 5.1 cm.

*Number of canes/hill*.—5 to 6.

*Cane color*.—Base — RHS 144B; Middle and tip — RHS 144A.

*Spines*.—Present.

*Spine density*.—Base: 6.0/cm$^2$ | Middle: 10.1/cm$^2$ | Tip: 5.1/cm$^2$.

*Spine shape*.—Acuminate.

*Spine length*.—0.14 cm.

*Spine width*.—0.14 cm.

*Spine apex descriptor*.—Acuminate.

*Spine color*.—RHS 187A.

*Vegetative bud shape*.—Rounded.

*Vegetative bud length*.—1.1 cm.

*Vegetative bud diameter* (*base*).—0.8 cm.

*Vegetative bud diameter* (*tip*).—0.06 cm.

*Vegetative bud color*.—RHS 143A.

Floricanes:

*Cane diameter*.—Base — 1.4 cm | Middle — 1.3 cm | Tip — 1.2 cm.

*Cane length*.—93.6 cm.

*Number of nodes per cane*.—20. Internode Length: Base — 4.8 cm | Middle — 5.9 cm | Tip — 3.5 cm.

*Cane color*.—Lower Cane — RHS 166A | Upper Cane — RHS 164A.

*Spines*.—Present. Spine density: Base: 5/cm$^2$ | Middle: 4/cm$^2$ | Tip: 4/cm$^2$. Spine shape: Acuminate. Spine length: 0.08 cm. Spine width: 0.01 cm. Spine apex descriptor: Acuminate. Spine color: RHS 166C.

*Reproductive bud shape*.—Rounded.

*Reproductive bud length*.—1.2 cm.

*Reproductive bud diameter* (*base*).—0.7 cm.

*Reproductive bud diameter* (*tip*).—0.06 cm.

*Reproductive bud color*.—RHS 143A.

*Reproductive bud texture*.—Pubescent.

*Winter hardiness*.—Unknown outside of USDA Hardiness Zone 9b (Watsonville, Calif.). This cultivar is best adapted to the mild coastal conditions of California.

*Drought/heat tolerance*.—Pollen viability and fruit quality of raspberry generally begins to decline above 30° C. This is consistent with observations of 'PBBrasp1381'. Raspberries are generally not drought tolerant, and 'PBBrasp1381' has not been tested in unirrigated plots.

Leaves:

*Complete leaf*.—Length: 17.1 cm. Width: 22.0 cm. Number of leaflets: 3 to 5.

*Terminal leaflet*.—Size Length: 13.8 cm. Width: 8.1 cm. Length/Width ratio: 1.7 cm. Leaf shape of apex: Acuminate. Leaf shape of base: Cordate. Leaf margin: Serrate. Leaf texture: Rigid interveinal puckering. Number of serrations per leaf: 78 serrations. Leaf shape of serrations: Flexuous — Flexuous. Leaf color: Upper Surface: RHS N137C. Lower Surface: RHS 144D. Leaf venation pattern: Palmate. Leaf venation color: Upper surface: RHS N137C. Lower surface: RHS N144D. Leaf pubescence density: Present on underside only; moderate. Color of leaf pubescence: RHS N138C. Shape of leaf in cross-section: Oval. Number of leaflets/leaf: Primocane: 3-5. Floricane: 3. Interveinal blistering within leaf: Present. Leaf glossiness: Matte.

*Primocane leaves*.—Petiole length: 7.7 cm. Petiole diameter: 2.2 cm. Petiole Color: Upper: RHS 144B. Lower: RHS 144C. Rachis length: 4.0 cm. Stipule length: 0.93 cm. Stipules per leaf: 2. Stipule Width: 0.007 cm. Stipule Color: Upper Surface: RHS 144C. Lower Surface: RHS 144C.

*Terminal leaflet*.—Length: 10.7 cm. Width: 8.3 cm. Rachis length: 3.6 cm.

*Distal lateral leaflet*.—Length: 8.2 cm. Width: 3.6 cm. Petiolule length: Sessile.

*Basal lateral leaflet*.—Length: 10.1 cm. Width: 6.7 cm. Petiolule length: 0.5 cm.

*Floricane leaves*.—Petiole length: 5.2 cm. Stipule length: 0.8 cm. Stipules per leaf: 2. Stipule Width: 0.006 cm. Stipule Color: Color Upper surface: RHS 144B. Lower surface: RHS 144B.

*Terminal leaflet*.—Length: 13.8 cm. Width: 8.1 cm. Rachis length: 2.3 cm. Distal lateral leaflet: Not Present. Length: N/A. Width: N/A.

*Petiolule*.—Length: N/A. Diameter: N/A. Color: N/A.

*Basal lateral leaflet*.—Length: 11.3 cm. Width: 5.4 cm.

*Petiolule*.—Sessile. Length: N/A. Diameter: N/A. Color: Upper: N/A. Lower: N/A.

Flowers:

*Time of flowering* (*50% of plants at first flower*).—Approximately 100 days after planting (on primocanes).

*Flower size*.—Length: 0.6 cm. Diameter: 0.9 cm.

*Fragrance*.—None.

*Peduncle*.—Length: 5.6 cm. Diameter: 0.2 cm. Color: RHS 143C. Pubescence: Present. Texture: Smooth, with few spines.

*Perianth*.—Flowering trusses shape: Truncate.

*Petals*.—Color: Upper — RHS 157B | Lower — RHS 157C. Number per flower: 5 petals. Shape: Obovate. Length: 0.9 cm. Width: 0.3 cm. Apex descriptor: Rounded. Base Descriptor: Cuneate. Margin descriptor: Entire. Texture: Smooth with visible striations.

*Sepals*.—Quantity: 5 sepals. Length: 0.9 cm. Width: Base — 0.6 cm | Mid — 0.4 cm | Tip — 0.0 cm. Color: RHS 143C. Apex descriptor: Acuminate. Margin descriptor: Entire. Texture: Pubescent.

*Pedicel*.—Color: RHS 143C. Length: 2.2 cm. Diameter: 0.2 cm.

Reproductive organs: Self-fertile: Yes.

*Male*.—Stamen Number: 105. Filament Length: 0.5 cm. Diameter: 0.01 cm. Color: RHS 157A. Anther Length: 0.005 cm. Diameter: 0.004 cm. Color: RHS 199A. Pollen Color: RHS 199A. Amount: Moderate.

*Female*.—Style Length: 0.03 cm. Diameter: 0.006 cm. Color: RHS 157A. Stigma Length: 0.3 cm. Diameter: 0.009 cm. Color: RHS 157A. Ovary Length: 0.01 cm. Diameter: 0.07 cm. Color: N144D.

Fruit:

*Predominant shape*.—Broad Conical.

*Weight* (g).—6.2 g.

*Length*.—2.9 cm.

*Width*.—Base — 2.1 cm | Mid — 1.6 cm | Tip — 1.1 cm.

*Length/width ratio*.—1.8 cm.

*Receptacle*.—Length: 1.4 cm. Diameter: Base — 0.5 cm | Mid — 0.3 cm | Tip — 0.1 cm. Color: RHS 10C.

*Drupelet*.—Length: 0.6 cm. Diameter: 0.3 cm. Number: 114. Weight: 0.05 g.

*Fruit color*.—External: RHS 46B. Internal: RHS 182A.

*Firmness of skin*.—Very firm.

*Firmness of flesh*.—Firm.

*Hollow center*.—Present.

*Number of fruit per node*.—9.

*Time of ripening* (*50% of plants with first fruit*).—135 days after planting, on average.

*Time of fruiting*.—Spring to summer on floricanes; late summer and early autumn on primocanes.

*Type of bearing*.—Remontant.

*Fruit yield*.—23,483 lb/a, on average.

*Average brix*.—9.9.

*Typical market use*.—Fresh.

*Keeping quality*.—Excellent.

*Shipping quality*.—Excellent.

Pest and disease resistance: 'PBBrasp1381' shows resistance to yellow rust (*Phragmidium rubi-idaei*), a common fungal disease under commercial conditions. 'PBBrasp1381' has exhibited field tolerance to Raspberry Bushy Dwarf Virus (RBDV) and *Phytophthora* root rot.

What is claimed is:

1. A new and distinct cultivar of Raspberry plant named 'PBBrasp1381' as described and shown herein.

* * * * *